United States Patent
Wagstaff et al.

(10) Patent No.: US 11,364,256 B2
(45) Date of Patent: Jun. 21, 2022

(54) VIRAL INHIBITION

(71) Applicants: Monash University, Clayton (AU); Melbourne Health, Parkville (AU)

(72) Inventors: Kylie Michelle Wagstaff, Melbourne (AU); Leon Caly, Melbourne (AU); David Jans, Melbourne (AU)

(73) Assignees: Monash University, Victoria (AU); Melbourne Health, Victoria (AU)

( * ) Notice: Subject to any disclaimer, the term of this patent is extended or adjusted under 35 U.S.C. 154(b) by 0 days.

(21) Appl. No.: 17/201,621

(22) Filed: Mar. 15, 2021

(65) Prior Publication Data
US 2021/0283160 A1 Sep. 16, 2021

(30) Foreign Application Priority Data

Mar. 13, 2020 (AU) ................................ 2020900778
May 14, 2020 (AU) ................................ 2020901549

(51) Int. Cl.
*A61K 31/7048* (2006.01)
*A61K 31/365* (2006.01)

(52) U.S. Cl.
CPC ........ *A61K 31/7048* (2013.01); *A61K 31/365* (2013.01)

(58) Field of Classification Search
CPC . A61K 31/7048; A61K 31/366; A61K 31/365
See application file for complete search history.

(56) References Cited

U.S. PATENT DOCUMENTS

| | | | | |
|---|---|---|---|---|
| 7,544,712 B1 * | 6/2009 | Hsu | ........................ | A61K 31/33 514/485 |
| 8,313,752 B2 * | 11/2012 | Razzak | .................. | A61K 47/26 424/215.1 |
| 8,741,856 B2 | 6/2014 | Milani De Mayo De Mari | | |
| 2012/0208778 A1 | 8/2012 | Milani De Mayo De Mari | | |

FOREIGN PATENT DOCUMENTS

| | | |
|---|---|---|
| EP | 2327410 A1 | 6/2011 |
| IN | 04529CN2012 | 2/2014 |
| WO | 2011051159 A1 | 5/2011 |

OTHER PUBLICATIONS

American Society of Health-System Pharmacists, "Assessment of Evidence for COVID-19-Related Treatments: Updated Apr. 19, 2021"; available at https://www.ashp.org/-/media/8CA43C674C6D4335B6A19852843C4052.ashx (Year: 2021).*
fda.gov from the United States Food & Drug Administration, "Why you should not use ivermectin to treat or prevent COVID-19"; Updated Mar. 5, 2021; available at https://www.fda.gov/consumers/consumer-updates/why-you-should-not-use-ivermectin-treat-or-prevent-covid-19 (Year: 2021).*
Schmith, V. D. et al., Clinical Pharmacology & Therapies, "The approved dose of ivermectin alone is not the ideal dose for the treatment of COVID-19", first published May 2020 (Year: 2020).*
Shen, L. et al., Journal of Virology, "High-Throughput Screening and Identification of Potent Broad-Spectrum Inhibitors of Coronaviruses", 2019, vol. 93, No. 12, 15 pages (Year: 2019).*
Product Information for Stromectol® Tablets, Merck Sharp Dohme (Australia) [retrieved from internet on Mar. 30, 2021] <URL:https://www.tga.gov.au/sites/default/files/auspar-ivermectin-131030-pi.pdf>, Published Oct. 30, 2013, Description, Clinical Trials and Indications (16 pages).
"Prescribing information for Moxidectin tablets", Medicines Development for Global Health [retrieved from internet on Mar. 30, 2021] <URL:https://www.accessdata.fda.gov/drugsatfda_docs/label/2018/210867lbl.pdf>, Published Jun. 2018 Indications and Usage, Description and Clinical Studies (12 pages).
"Freedom of Information Summary, NADA 141-519, ProHeart 12 (moxidectin) Dogs," Zoetis Inc [retrieved from internet on Mar. 30, 2021] URL:https://animaldrugsatfda.fda.gov/adafda/app/search/public/document/downloadFoi/7307>, Published Jul. 2, 2019 General Information, Substantial Evidence and Clinical Field Study (20 pages).
"Ivermectin and COVID-19 Evidence Check", NSW Health [retrieved from internet on Mar. 30, 2021] <URL:https://aci.health.nsw.gov.au/_data/assets/pdf file/0004/625090/20201223-Evidence-Check-Ivermectin-and-COVID-19.pdf> Published Dec. 23, 2020 (18 pages).
"EMA advises against use of ivermectin for the prevention or treatment of COVID-19 outside randomized clinical trials", European Medicines Agency [retrieved from internet on Mar. 30, 2021] <URL: https://www.ema.europa.eu/en/news/ema-advises-against-use-ivermectin-prevention-treatment-covid-19-outside-randomised-clinical-trials> Published Mar. 22, 2021 (5 pages).
Bryan et al., "Detection of equine coronavirus in horses in the United Kingdom", Vet Rec 184(4):123 (2 pages).
Caly et al., 2020 "The FDA-approved drug ivermectin inhibits the replication of SARS-CoV-2 in vitro," Antiviral Res 178 (2020) 104787 (4 pages).
Chaccour et al., 2021 "The effect of early treatment with ivermectin on viral load, symptoms and humoral response in patients with non-severe COVID-19: A pilot, double-blind, placebo-controlled, randomized clinical trial," EClinicalMedicine 32 100720 (9 pages).
Crump, 2017 "Ivermectin: enigmatic multifaceted 'wonder' drug continues to surprise and exceed expectations", The Journal of Antibiotics 70:495-505, p. 500—"Antiviral (e.g. HIV, Dengue, encephalitis)".
De Wilde et al., 2014 "Screening of an FDA-Approved Compound Library Identifies Four Small-Molecule Inhibitors of Middle East Respiratory Syndrome Coronavirus Replication in Cell Culture," Antimicrob Agents Chemother 58 (8):4875-84.

(Continued)

*Primary Examiner* — Bahar Craigo
(74) *Attorney, Agent, or Firm* — Dechert LLP; Andrea L. C. Reid; Todd K. Macklin

(57) ABSTRACT

The technology relates to the use of at least one macrocyclic lactone such as ivermectin or moxidectin to inhibit a coronavirus in a subject in order to treat, prevent or reduce the risk of infection by the coronavirus.

30 Claims, 8 Drawing Sheets

(56) References Cited

OTHER PUBLICATIONS

Wagstaff et al., 2012 "Ivermectin is a specilc inhibitor of importin α/β-mediated nuclear import able to inhibit replication of HIV-1 and dengue virus," Biochem J 443:851-56.
International Search Report dated Apr. 13, 2021 corresponding to related International Patent Application No. PCT/AU2021/050218 (5 pages).
Written Opinon dated Apr. 13, 2021 corresponding to related International Patent Application No. PCT/AU2021/050218 (7 pages).

* cited by examiner

VIRAL INHIBITION

1. REFERENCE TO RELATED APPLICATION

This application claims priority to Australian provisional patent application number 2020900778 filed 13 Mar. 2020, and Australian provisional patent application number 2020901549 filed 14 May 2020. These applications are incorporated by cross-reference in their entireties.

2. TECHNICAL FIELD

The technology relates to the use of macrocyclic lactones to inhibit a coronavirus. In particular, the technology relates to the use of macrocyclic lactones such as ivermectin and/or moxidectin to inhibit a coronavirus or to prevent or treat an infection by the coronavirus in a subject in need thereof.

3. BACKGROUND

As of 14 Feb. 2020, more than 64,000 people worldwide were infected by severe acute respiratory syndrome coronavirus 2 (SARS-CoV-2). By early March 2021 the World Health Organization's "COVID-19 Weekly Epidemiological Update" reported that the global number of cumulative SARS-CoV-2 infections was over 110,000,000. SARS-CoV-2 is the causative agent of the 2019 outbreak of coronavirus disease (COVID-19) which has a death rate of about 2.4-5%. COVID-19 has resulted in an unprecedented worldwide public health response. With no approved antiviral agents or vaccines available, the response has been limited to symptomatic treatment and monitoring and containment/isolation of infected patients.

Ivermectin is macrocyclic lactone approved by the FDA as a broad spectrum anti-parasitic agent that in recent years has been shown to have potent anti-viral activity against a broad range of viruses. Originally identified as an inhibitor of interaction between the human immunodeficiency virus-1 (HIV-1) integrase protein (IN) and the importin (IMP) $\alpha/\beta 1$ heterodimer responsible for IN nuclear import, Ivermectin has since been confirmed to inhibit IN nuclear import and HIV-1 replication. Other actions of ivermectin have been reported, but ivermectin has been shown to inhibit nuclear import of host and viral proteins, including simian virus SV40 large tumour antigen (T-ag) and Dengue virus non-structural protein 5 (DENV NS5). Ivermectin has been demonstrated to limit infection by viruses such as DENV, Venezuelan equine encephalitis virus (VEEV) and influenza, by a mechanism believed to be due to the reliance of RNA viruses on IMP $\alpha/\beta 1$ during infection.

Moxidectin is another example of a macrocyclic lactone. Moxidectin is and FDA approved medication for the treatment of treatment of onchocerciasis in humans. It is also used in animals as an anti-parasitic in the prevention, treatment or control of helminthic, ectoparasitic, insect, acarid and nematode infections and infestations. It is especially useful to control such parasites as ticks and worms in cattle and sheep. Moxidectin may be administered to livestock and other animals in a number of ways including, as a topical or "drench", as a subcutaneous injection, or orally in pill or tablet form. Moxidectin has been demonstrated to limit infection by viruses such as influenza H9.

Many coronaviruses have a nucleocapsid protein that is located in the nucleus of the host cell and it is thought that IMP $\alpha/\beta 1$ plays a role in nuclear import of this protein. However, the nucleocapsid protein of SARS-CoV (which is essentially identical to the nucleocapsid protein of SARS-CoV-2) is almost completely located in the cytoplasm. In addition, the ORF6 protein of SARS-CoV binds IMP $\alpha/\beta 1$ and sequesters it in the cytoplasm and prevents the infected host cell from mounting an antiviral response via the STAT1 transcription factor which requires IMP $\alpha/\beta 1$ to enter the nucleus. Accordingly, IMP $\alpha/\beta 1$ inhibitors such as ivermectin would be expected to release the IMP $\alpha/\beta 1$ from ORF6 but this would also lead to inhibition of the STAT 1 induced antiviral response consequently exacerbating the infection.

In contrast to the expected effect, the inventors have identified that ivermectin and moxidectin can inhibit SARS-CoV-2 and these macrocyclic lactones are therefore useful to treat and prevent infection by SARS-CoV-2 and all members of the Coronaviridae (Coronavirus) family.

4. SUMMARY

In a first aspect there is provided a formulation comprising at least one macrocyclic lactone or a salt, hydrate, solvate, tautomer or stereoisomer thereof, for use as an inhibitor of a coronavirus in a subject.

The at least one macrocyclic lactone may be an avermectin, a milbemycin, or both.

The avermectin may be selected from abamectin, dimadectin, doramectin, emamectin, eprinomectin, ivermectin, latidectin, lepimectin, and selamectin, preferably avermectin is ivermectin.

The milbemycin may be selected from milbemectin, milbemycin D, milbemycin oxime, moxidectin, and nemadectin. Preferably the milbemycin is moxidectin.

In one embodiment the avermectin is ivermectin and the milbemycin is moxidectin.

In some embodiments the subject is a dog, cat, horse, cow, sheep, camel, chicken or pig, preferably the subject is a human.

The coronavirus may be coronavirus 229E, coronavirus NL63, coronavirus OC43, SARS-CoV, MERS-CoV, SARS-CoV-2, or variants thereof, preferably SARS-CoV-2 or a variant thereof.

In a second aspect there is provided a method of inhibiting a coronavirus in a subject or treating a subject with a coronavirus infection, the method comprising administering a therapeutically effective amount of at least one macrocyclic lactone or a salt, hydrate, solvate, tautomer or stereoisomer thereof to the subject The level of detectable coronavirus in the subject may be reduced by at least 50%, for example the level of detectable coronavirus in the subject is reduced by at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or at least 99.9%.

The level of detectable coronavirus may be reduced over a period of 1, 2, 3, or more days after administration of the macrocyclic lactone or a salt, hydrate, solvate, tautomer or stereoisomer thereof.

The at least one macrocyclic lactone may be an avermectin and/or a milbemycin.

The avermectin is selected from abamectin, dimadectin, doramectin, emamectin, eprinomectin, ivermectin, latidectin, lepimectin, and selamectin, preferably the avermectin is ivermectin.

The milbemycin may be selected from milbemycin D, milbemycin oxime, moxidectin, and nemadectin, preferably the milbemycin is moxidectin.

In one embodiment the avermectin is ivermectin and the milbemycin is moxidectin.

In some embodiments the subject is a dog, cat, horse, cow, sheep, camel, chicken or pig, preferably the subject is a human.

The coronavirus may be coronavirus 229E, coronavirus NL63, coronavirus OC43, SARS-CoV, MERS-CoV, SARS-CoV-2, or variants thereof, preferably SARS-CoV-2 or a variant thereof.

The at least one macrocyclic lactone may be administered at a dose of about 0.1 mg/kg to about 1.0 mg/kg body weight of the subject.

In a third aspect there is provided a method of preventing or reducing the risk of a coronavirus infection, or preventing antibody dependent enhanced (ADE) coronavirus infection in a subject, comprising administering a therapeutically effective amount of at least one macrocyclic lactone, or a salt, hydrate, solvate, tautomer or stereoisomer thereof to the subject.

The at least one macrocyclic lactone may be an avermectin and/or a milbemycin.

The avermectin is selected from abamectin, dimadectin, doramectin, emamectin, eprinomectin, ivermectin, latidectin, lepimectin, and selamectin, preferably the avermectin is ivermectin.

The milbemycin may be selected from milbemycin D, milbemycin oxime, moxidectin, and nemadectin, preferably the milbemycin is moxidectin.

In one embodiment the avermectin is ivermectin and the milbemycin is moxidectin.

In some embodiments the subject is a dog, cat, horse, cow, sheep, camel, chicken or pig, preferably the subject is a human.

The coronavirus may be coronavirus 229E, coronavirus NL63, coronavirus OC43, SARS-CoV, MERS-CoV, SARS-CoV-2, or variants thereof, preferably SARS-CoV-2 or a variant thereof.

The at least one macrocyclic lactone may be administered at a dose of about 0.1 mg/kg to about 1.0 mg/kg body weight of the subject.

In a fourth aspect there is provided use of at least one macrocyclic lactone or a salt, hydrate, solvate, tautomer or stereoisomer thereof, for the manufacture of a medicament for the prevention or treatment of a coronavirus infection.

In a fifth aspect, there is provided use of at least one macrocyclic lactone or a salt, hydrate, solvate, tautomer or stereoisomer thereof, for the manufacture of a medicament for reducing the risk of acquiring a coronavirus infection.

In a sixth aspect, there is provided use of at least one macrocyclic lactone or a salt, hydrate, solvate, tautomer or stereoisomer thereof for the preparation of a medicament for preventing ADE coronavirus infection in a subject.

5. BRIEF DESCRIPTION OF THE DRAWINGS

FIG. 1 illustrates the relative amount of viral RNA associated with (A) Vero/hSLAM cells with infected with SARS-CoV-2 isolate or (B) in the cell supernatant before and 1, 2, and 3 days after treatment with 5 μM ivermectin. (C, D) Based on detection of the E gene, a >5000 reduction in viral RNA was observed in both supernatant and cell pellets from samples treated with 5 μM ivermectin at 48 h. (E, F) Nearly identical results were obtained using primers specific for the SARS-CoV-2 RdRp gene.

FIG. 2 illustrates that ivermectin and moxidectin strongly inhibit replication of the SARS-CoV-2 clinical isolate Australia/VIC01/2020. (A) Ivermectin and moxidectin reduce viral RNA in in culture supernatants from Vero/hSLAM cells infected with SARS-CoV-2 clinical isolate Australia/VIC01/2020. (B-D) Ivermectin and moxidectin reduce viral RNA in culture supernatants from Vero/hSLAM cells infected were infected with SARS-CoV-2 clinical isolate Australia/VIC01/2020 prior to addition of vehicle (DMSO), ivermectin (solid squares) or moxidectin (open squares). Supernatant were analysed for the SARS-CoV-2 E gene at 24 h (B), 48 h (C), or 72 h (D).

Figure 6:
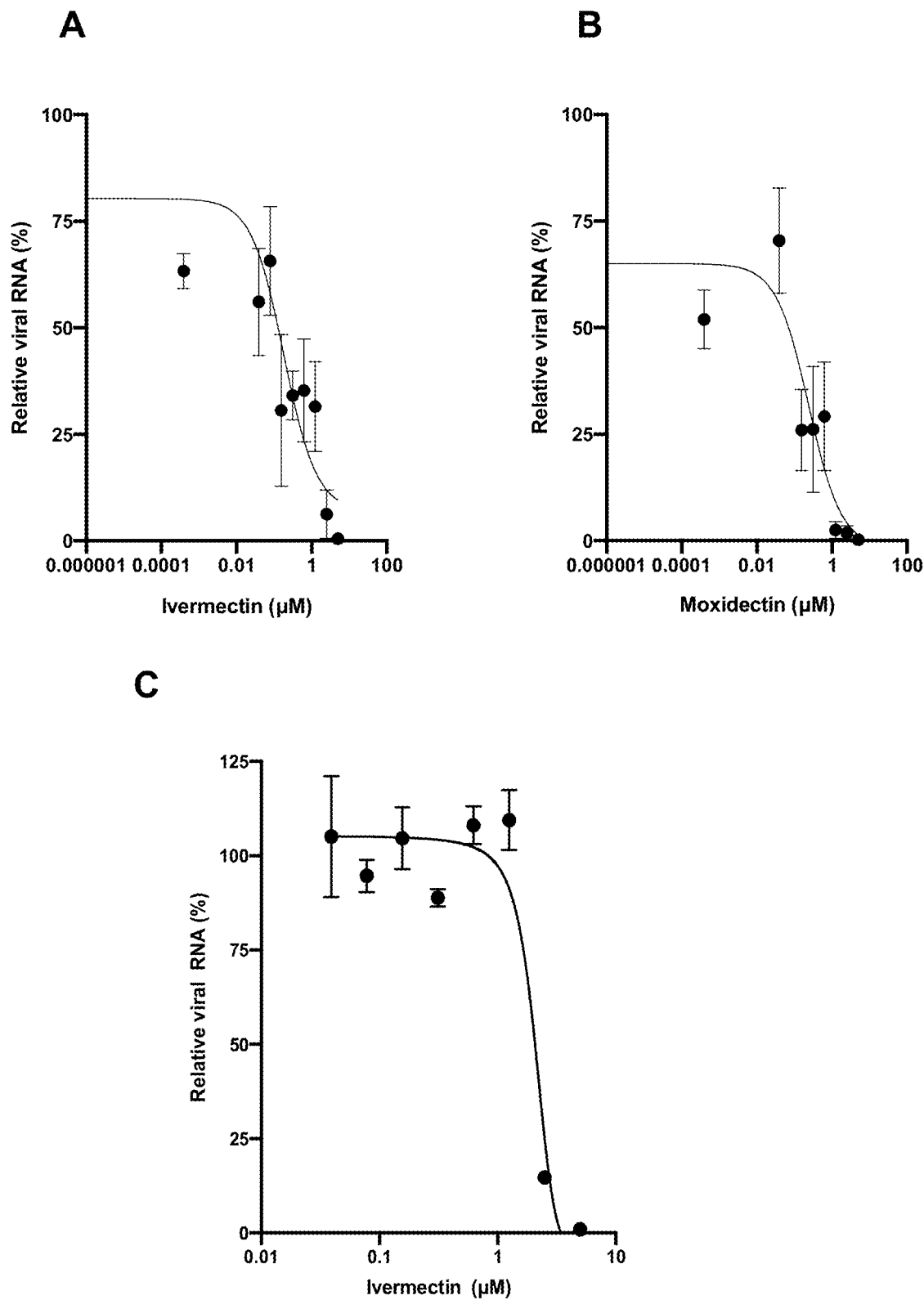

FIG. 6 illustrates that ivermectin and moxidectin are effective anti-viral inhibitors of the seasonal coronavirus 229E. Huh-7 cells were infected with 229E prior to addition of vehicle (DMSO), ivermectin (A) or moxidectin (B) at the indicated concentrations. Three parameter dose response curves were fitted using GraphPad prism to determine $IC_{50}$ values. (C) For assessment of prophylactic potential Huh-7 cells were pre-treated with DMSO or ivermectin at the indicated concentrations prior to infection with 229E in the presence of DMSO or ivermectin. Samples were washed post-adsorption and incubated in the fresh media containing DMSO or ivermectin for 48 h before quantitation of viral load.

6. DETAIL DESCRIPTION

6.1. Definitions

Throughout this specification, unless the context clearly requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, the term "consisting of" means consisting only of.

The term "consisting essentially of" means the inclusion of the stated element(s), integer(s) or step(s), but other element(s), integer(s) or step(s) that do not materially alter or contribute to the working of the invention may also be included. Thus, in the context of the present invention a composition "consisting essentially of" a specified macrocyclic lactone means that the specified macrocyclic lactone is the active agent and the composition does not include other (unspecified) active agent(s) in quantities that will have a therapeutic effect. However, those skilled in the art will understand that it is possible that de minimis amounts of other compounds (e.g., other macrocyclic lactones) may be present, e.g., as impurities. The composition may include inert components such as excipients, diluents and the like, even if those components are not expressly identified.

Any discussion of documents, acts, materials, devices, articles or the like which has been included in the present specification is solely for the purpose of providing a context for the present technology. It is not to be taken as an admission that any or all of these matters form part of the prior art base or were common general knowledge in the field relevant to the present technology as it existed before the priority date of each claim of this specification.

Unless the context requires otherwise or specifically stated to the contrary, integers, steps, or elements of the technology recited herein as singular integers, steps or elements clearly encompass both singular and plural forms of the recited integers, steps or elements.

In the context of the present specification the terms "a" and "an" are used to refer to one or more than one (i.e., at least one) of the grammatical object of the article. By way of example, reference to "an element" means one element, or more than one element.

In the context of the present specification the term "about" means that reference to a figure or value is not to be taken as an absolute figure or value but includes margins of variation above or below the figure or value in line with what a skilled person would understand according to the art, including within typical margins of error or instrument limitation. In other words, use of the term "about" is understood to refer to a range or approximation that a person or skilled in the art would consider to be equivalent to a recited value in the context of achieving the same function or result.

The terms "treating", and "treatment" are used herein to refer to curative therapy, prophylactic therapy, palliative therapy and preventative therapy. Thus, in the context of the present disclosure the term "treating" encompasses curing, ameliorating or tempering the severity of a coronavirus infection or one or more of its associated symptoms.

The terms "effective amount" or "therapeutically effective amount" refer to an amount of macrocyclic lactone sufficient to produce a desired therapeutic or pharmacological effect in the subject being treated. The terms are synonymous and are intended to qualify the amount of each macrocyclic lactone that will achieve the goal of improvement in disease severity and/or the frequency of incidence over treatment of each macrocyclic lactone by itself while preferably avoiding or minimising adverse side effects, including side effects typically associated with other therapies. Those skilled in the art can determine an effective dose using information and routine methods known in the art.

More specifically, the terms "effective amount" or "therapeutically effective level" and similar terms means an amount of a macrocyclic lactone that (i) treats the particular disease, condition, or disorder, (ii) attenuates, ameliorates, or eliminates one or more symptoms of the particular disease, condition, or disorder, (iii) prevents or delays the onset of one or more symptoms of the particular disease, condition, or disorder described herein, (iv) prevents or delays progression of the particular disease, condition or disorder, or (v) reverses damage caused prior to treatment to some extent. The reversal does not have to be absolute. The amount administered may be higher than what is required within the body to achieve the therapeutic effect, but takes in to account the absorption, distribution, metabolism and excretion (ADME) profile of the macrocyclic lactone, the route of administration and the administration frequency.

In an alternative embodiment, the severity of symptoms associated with a coronavirus infection, can be reduced by administering a therapeutically effective amount of a macrocyclic lactone to the subject. Reducing symptom severity means that one or more symptoms are attenuated, ameliorated, or eliminated, or the onset of one or more symptoms is prevented or delayed.

A "pharmaceutical carrier, diluent or excipient" includes, but is not limited to, any physiological buffered (i.e., about pH 7.0 to 7.4) medium comprising a suitable water soluble organic carrier, conventional solvents, dispersion media, fillers, solid carriers, coatings, antibacterial and antifungal agents, isotonic and absorption delaying agents. Suitable water soluble organic carriers include, but are not limited to, saline, dextrose, corn oil, dimethylsulfoxide, and gelatin capsules. Other conventional additives include lactose, mannitol, corn starch, potato starch, binders such as microcrystalline cellulose, cellulose derivatives such as hydroxypropylmethylcellulose, acacia, gelatins, disintegrators such as sodium carboxymethylcellulose, and lubricants such as talc or magnesium stearate.

"Subject" includes any human or non-human mammal Thus, in addition to being useful for human treatment, the compounds of the present invention may also be useful for veterinary treatment of mammals, including companion animals and farm animals, such as, but not limited to dogs, cats, horses, cows, sheep, camels, chickens and pigs. In preferred embodiments the subject is a human.

In the context of this specification the term "administering" and variations of that term including "administer" and "administration", includes contacting, applying, delivering or providing a compound or composition of the invention to a subject by any appropriate means.

The term "inhibit" as used herein in connection with a coronavirus refers to a decrease in binding of a protein encoded by a coronavirus to a cellular target, a decrease in disease symptoms or severity, or a decrease in viral load.

Those skilled in the art will appreciate that the technology described herein is susceptible to variations and modifications other than those specifically described. It is to be understood that the technology includes all such variations and modifications. For the avoidance of doubt, the technology also includes all of the steps, features, and compounds referred to or indicated in this specification, individually or collectively, and any and all combinations of any two or more of said steps, features and compounds.

6.2. Description of Embodiments

The present inventors have identified that the macrocyclic lactones ivermectin and moxidectin can be used to inhibit SARS-CoV-2. In particular, ivermectin and moxidectin reduce SARS-CoV-2 viral load and can therefore be used to treat, reduce or prevent infection.

Accordingly, there is provided the use of at least one macrocyclic lactone to inhibit a coronavirus in a subject. The macrocyclic lactone can be used to treat and/or prevent a coronavirus infection, this entails one or more of the following:

i) reducing viral load in a subject infected with a coronavirus including but not limited to SARS, MERS, SARS-CoV-2, and in particular, a subject infected with any isolate or strain of SARS-CoV-2.

ii) reducing or ameliorating the risk to a subject of infection with a coronavirus including but not limited to SARS, MERS, SARS-CoV-2, and in particular, the risk of infection with any isolate or strain of SARS-CoV-2.

iii) alleviating symptoms of a coronavirus infection in a subject, having or suspected of having a coronavirus infection including but not limited to SARS, MERS, SARS-CoV-2, and in particular, an infection by any isolate or strain of SARS-CoV-2.

iv) reducing or ameliorating the risk of ADE coronavirus infection in a subject having had or suspected of having had a previous coronavirus infection.

Alternatively, the patient may also be receiving other treatments, such that the macrocyclic lactones or compositions thereof are administered in an adjunct therapy. Additional therapies may be those that treat the accompanying symptoms including, without limitation, pain relief such as aspirin, acetaminophen, codeine, and nonsteroidal anti-inflammatory drugs (NSAIDS). In this regard, there is provided a method of treating a coronavirus infection, or a method of reducing symptom severity in a patient having or suspected of having a coronavirus infection, comprising administering an effective amount of at least one macrocyclic lactone to a subject in need thereof, together with another therapeutic, wherein the macrocyclic lactone administered achieves a therapeutically effective level in the subject.

The methods and uses described herein comprise the administration of at least one macrocyclic lactone, or a formulation comprising at least one macrocyclic lactone to a subject exposed to a coronavirus, infected by a coronavirus, or a subject suspected of exposure to a coronavirus.

Administration of a macrocyclic lactone to a subject inhibits a coronavirus in the subject. The inhibition has a number of beneficial effects such as reducing viral load, preventing or reducing the interaction of the coronavirus with cellular targets such as IMP α/β1 which in turn prevents or reduces infection of a cell by the coronavirus. These effects of viral inhibition are useful to prevent or treat (e.g., lessen the severity) of a coronavirus infection.

As noted above the inhibition of coronavirus by a macrocyclic lactone can prevent or reduce the interaction of the coronavirus with a cellular target such as IMP α/β1 and this in turn can reduce or prevent infection of the cell by the coronavirus, accordingly, administration of a macrocyclic lactone to a subject reduces the risk of a coronavirus infection.

The macrocyclic lactone can be administered as a precautionary measure for example to healthcare workers, caregivers, or those at risk of exposure to a coronavirus.

While infection by one coronavirus serotype or strain may be protective of re-infection by the same serotype or strain, the subject may not be protected by infection with other serotypes or strains. Subsequent infection with a different serotype is thought to result in antibody-dependent enhancement (ADE) of infection. Accordingly, in some embodiments of the invention, the subject has had a prior coronavirus infection for example with a different coronavirus serotype or strain. These subjects are at higher risk of ADE coronavirus infection. The methods of the invention are also suitable for treating, preventing or reducing the risk of ADE coronavirus infection.

ADE occurs when circulating antibodies from a previous infection with a different coronavirus serotype lead to increased viral load, caused by cross-reactive but non-neutralising antibodies. ADE is known to occur with SARS-CoV and MERS-CoV. ADE also results in the increased expression of genes such as those encoding the cytokines interleukin (IL) 8 and tumor necrosis factor (TNF) α which are associated with development of more severe manifestations of an infection.

Accordingly, in a further embodiment of the invention, there is provided a method for preventing or reducing the severity of an ADE coronavirus infection, comprising administering an effective amount of a macrocyclic lactone.

There is also provided a use of an effective amount of a macrocyclic lactone in the preparation of a medicament for preventing ADE coronavirus infection in a subject in need thereof.

In some embodiments, administration of at least one macrocyclic lactone to a subject with a coronavirus infection reduces the amount of detectable coronavirus (cell associated or free virus) by at least 50%. For example, the amount of detectable coronavirus may be reduced by at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or at least 99.9%.

The level of detectable coronavirus may be reduced over a period of 1, 2, 3, or more days.

The $IC_{50}$ for a macrocyclic lactone is the concentration of macrocyclic lactone where the response (reduction of detectable coronavirus) is reduced by half. In some embodiments the macrocyclic lactone has an $IC_{50}$ less than about 10 μM. For example, the $IC_{50}$ may be less than 10 μM, 9 μM, 8 μM, 7 μM, 6 μM, 5 μM, 4 μM, 3 μM, 2 μM, or less than about 1 μM.

The macrocyclic lactones can be administered as a formulation comprising a pharmaceutically effective amount of the macrocyclic lactones, in association with one or more pharmaceutically acceptable excipients including carriers, vehicles and diluents. The term "excipient" herein means any substance, not itself a therapeutic agent, used as a diluent, adjuvant, or vehicle for delivery of a therapeutic agent to a subject or added to a pharmaceutical composition to improve its handling or storage properties or to permit or facilitate formation of a solid dosage form such as a tablet, capsule, or a solution or suspension suitable for oral, parenteral, intradermal, subcutaneous, or topical application. Excipients can include, by way of illustration and not limitation, diluents, disintegrants, binding agents, adhesives, wetting agents, polymers, lubricants, glidants, stabilizers, and substances added to mask or counteract a disagreeable taste or odor, flavors, dyes, fragrances, and substances added to improve appearance of the composition. Acceptable excipients include (but are not limited to) stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials, such as cellulose esters of alkanoic acids and cellulose alkyl esters, low melting wax, cocoa butter or powder, polymers such as polyvinyl-pyrrolidone, polyvinyl alcohol, and polyethylene glycols, and other pharmaceutically acceptable materials. Examples of excipients and their use is described in Remington's Pharmaceutical Sciences, 20th Edition (Lippincott Williams & Wilkins, 2000). The choice of excipient will to a large extent depend on factors such as the particular mode of administration, the effect of the excipient on solubility and stability, and the nature of the dosage form.

The macrocyclic lactones and pharmaceutical compositions of the invention may be formulated for oral, injectable, rectal, nasal, parenteral, subcutaneous, intravenous, topical, or intramuscular delivery. Non-limiting examples of particular formulation types include tablets, capsules, caplets, powders, granules, injectables, ampoules, vials, ready-to-use solutions or suspensions, lyophilized materials, creams, lotions, ointments, drops, suppositories and implants. Solid formulations such as the tablets or capsules may contain any number of suitable pharmaceutically acceptable excipients or carriers described above. The compounds of the invention may also be formulated for sustained delivery.

In one or more preferred embodiments the tablets and capsules for oral administration may be in unit dose presentation form, and may contain conventional excipients such as binding agents, for example, acacia, gelatin, sorbitol, tragacanth, or polyvinylpyrollidone; fillers, for example lactose, sugar, maize-starch, calcium phosphate, sorbitol or glycine; tabletting lubricants, for example, magnesium stearate, talc, polyethylene glycol or silica; disintegrants, for example, potato starch; or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example, sorbitol, methyl cellulose, glucose syrup, gelatin, hydroxyethyl cellulose, carboxymethyl cellulose, aluminum stearate gel or hydrogenated edible fats, emulsifying agents, for example, lecithin, sorbitan monooleate, or acacia; non-aqueous vehicles (which may include edible oils), for example, almond oil, oily esters such as glycerin, propylene glycol, or ethyl alcohol; preservatives, for example, methyl or propyl p hydroxybenzoate or sorbic acid; and, if desired, conventional flavouring or colouring agents.

For parenteral administration, including intravenous, intramuscular, subcutaneous, or intraperitoneal administration, fluid unit dosage forms may be prepared by combining the compound and a sterile vehicle, typically a sterile aqueous solution which is preferably isotonic with the blood of the recipient. Depending on the vehicle and concentration used, the compound may be either suspended or dissolved in the vehicle or other suitable solvent. In preparing solutions, the compound may be dissolved in water for injection and filter sterilized before filling into a suitable vial or ampoule and sealing. Advantageously, agents such as a local anesthetic, preservative and buffering agents can be dissolved in the vehicle. To enhance the stability, the composition may be frozen after filling into the vial and the water removed under vacuum. The dry lyophilized powder may then be sealed in the vial and an accompanying vial of water for injection or other suitable liquid may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. A surfactant or wetting agent may be included in the composition to facilitate uniform distribution of the compound.

Lyophilized formulations are preferably reconstituted with a solution consisting primarily of water (e.g., USP WFI, or water for injection) or bacteriostatic water (e.g., USP WFI with 0.9% benzyl alcohol). Alternatively, solutions comprising buffers and/or excipients and/or one or more pharmaceutically acceptable carriers may be used. The liquid that is to undergo freeze-drying or lyophilization preferably comprises all components desired in a final reconstituted liquid formulation.

In some embodiments, the composition of the invention is formulated in a sustained release formulation or depot. Exemplary sustained release formulations or depots include a microsphere; matrix; emulsion; lipid-based; polymer-based; nanomicelle; micelle; nanovesicle such as a liposome, noisome, transfersome, discome, pharmacosome, emulsome or spanlastic, especially a liposome; microparticle; nanoparticle such as a nanocapsule or nanosphere composed of e.g. lipids, proteins, natural or synthetic polymers such as albumin, sodium alginate, chitosan, PLGA, PLA and/or polycaprolactone; or in situ gel such as an in situ hydrogel drug delivery system.

The amount of therapeutically effective macrocyclic lactone that is administered and the dosage regimen for treating a disease condition with the compounds and/or pharmaceutical compositions of the present invention depends on a variety of factors, including the age, weight, sex, and medical condition of the subject, the severity of the disease, the route and frequency of administration, the particular compound employed, as well as the pharmacokinetic properties (e.g., adsorption, distribution, metabolism, excretion) of the individual treated, and thus may vary widely. Such treatments may be administered as often as necessary and for the period of time judged necessary by the treating physician. One of skill in the art will appreciate that the dosage regime or therapeutically effective amount of the compound to be administrated may need to be optimized for each individual. The pharmaceutical compositions may contain active ingredient in the range of about 0.1 mg to 2000 mg, typically in the range of about 0.5 mg to 500 mg, about 1 mg to 200 mg, about 1 mg to 100 mg and more typically between about 1 mg and 50 mg, for example.

A dose of about 0.01 mg/kg to 100 mg/kg body weight, or between about 0.1 mg/kg and about 50 mg/kg body weight, or between about 0.1 mg/kg and about 25 mg/kg body weight, or between about 0.1 mg/kg and about 10 mg/kg body weight, or between about 0.1 mg/kg, and about 1 mg/kg body weight may be appropriate, depending on the route and frequency of administration.

In one embodiment the dose of the macrocyclic lactone is about 0.1 mg/kg, 0.2 mg/kg, 0.3 mg/kg, 0.4 mg/kg, 0.5 mg/kg, 0.6 mg/kg, 0.8 mg/kg, 0.8 mg/kg, 0.9 mg/kg, or about 1 mg/kg body weight.

In some embodiments the amount of macrocyclic lactone administered is sufficient to achieve a plasma concentration of about 0.1 µM to about 100 µM, 0.1 µM to about 80 µM, 0.1 µM to about 60 µM, 0.1 µM to about 40 µM, 0.1 µM to about 20 µM, 0.1 µM to about 10 µM, or about 0.1 µM to about 5 µM.

In some embodiments the amount of macrocyclic lactone administered is sufficient to achieve a plasma concentration of about 1 ng/ml to about 500 ng/ml, 1 ng/ml to about 400 ng/ml, 1 ng/ml to about 300 ng/ml, 1 ng/ml to about 200 ng/ml, about 1 ng/ml to about 175 ng/ml, about 5 ng/ml to about 150 ng/ml, about 5 ng/ml to about 125 ng/ml, about 5 ng/ml to about 100 ng/ml, about 5 ng/ml to about 75 ng/ml, or about 5 ng/ml to about 50 ng/ml.

The compounds of the present invention may be administered along with a pharmaceutical carrier, diluent or excipient as described above. Alternatively, or in addition, the compounds may be administered in combination with other agents, for example, other antiviral agents and/or agents suitable for symptomatic relief such as pain killers or expectorants.

The terms "combination therapy" or "adjunct therapy" in defining use of a compound of the present invention and one or more other pharmaceutical agents, are intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations of each agent.

In accordance with various embodiments one or more macrocyclic lactones may be formulated or administered in combination with one or more other therapeutic agents. Thus, in accordance with various embodiments of the present invention, one or more macrocyclic lactones may be included in combination treatment regimens with other known treatments or therapeutic agents, and/or adjuvant or prophylactic agents.

A number of agents are available in commercial use, in clinical evaluation (e.g., amlodipine and losartan) and in pre-clinical development, which could be selected for treatment of coronavirus infection include antiviral agents such as protease inhibitors, helicase inhibitors, entry inhibitors. Other antiviral agents include oseltamivir (Tamiflu®), zanamivir (Relenza®), ribavirin, remdesivir, penciclovir, faviparvir, nafamostat, nitazoxanide, camostat mesylate, interferon α (e.g., interferon α B2), ritonavir, lopinavir, ASC09, azvudine, baloxavir marboxil, darunavir, cobicistat and chloroquine.

Other agents suitable for use in combination therapy are immune-based therapies including convalescent plasma, or monoclonal antibodies such as bamlanivimab, etesevimab, casirivimab, imdevimab (anti-SARS-CoV-2 spike protein monoclonal antibodies) or combinations thereof.

Other suitable agents which may be used in combination therapy (for example non-steroidal anti-inflammatories, acetaminophen, codeine, corticosteroids (such as dexamethasone), interferons, etc.) will be recognized by those of skill in the art. Suitable agents are listed, for example, in the Merck Index, An Encyclopaedia of Chemicals, Drugs and Biologicals, 12th Ed., 1996, and subsequent editions, the entire contents of which are incorporated herein by reference.

Combination regimens may involve the active agents being administered together, sequentially, or spaced apart as appropriate in each case. Combinations of active agents including compounds of the invention may be synergistic.

The co-administration of macrocyclic lactones may be effected by the macrocyclic lactone being in the same unit dose as another active agent, or the macrocyclic lactone and one or more other active agent(s) may be present in individual and discrete unit doses administered at the same, or at a similar time, or at different times according to a dosing regimen or schedule. Sequential administration may be in any order as required and may require an ongoing physiological effect of the first or initial compound to be current when the second or later compound is administered, especially where a cumulative or synergistic effect is desired.

The co-administration of macrocyclic lactones may be effected by the compounds being in the same unit dose as another active agent, or the compounds and one or more other active agent(s) may be present in individual and discrete unit doses administered at the same, or at a similar time, or at different times according to a dosing regimen or schedule. Sequential administration may be in any order as required and may require an ongoing physiological effect of the first or initial compound to be current when the second or later compound is administered, especially where a cumulative or synergistic effect is desired.

6.2.1. Coronavirus

As described herein at least one macrocyclic lactone can be used to inhibit a coronavirus in a subject. In addition, a macrocyclic lactone can be used to treat and/or prevent a coronavirus infection.

The methods and uses are applicable to all members of the Coronaviridae (Coronavirus) family.

For example, the coronavirus may be an alphacoronavirus such as coronavirus 229E, coronavirus NL63, porcine epidemic diarrhea coronavirus (PEDV), or swine acute diarrhea syndrome coronavirus (SADS-CoV).

In one embodiment the alphacoronavirus is coronavirus 229E, or coronavirus NL63.

In some embodiments the coronavirus may be a betacoronavirus such as murine coronavirus. In other embodiments the coronavirus is a betacoronavirus 1, for example coronavirus HKU1, murine coronavirus, SARS (severe acute respiratory syndrome)-coronavirus (SARS-CoV), Severe acute respiratory syndrome coronavirus 2 (SARS-CoV-2), MERS (Middle east respiratory syndrome) coronavirus (MERS-CoV), Middle East respiratory syndrome-related coronavirus, or coronavirus OC43.

In some embodiment the coronavirus is coronavirus OC43, SARS-CoV, MERS-CoV or SARS-CoV-2. In one embodiment the coronavirus is SARS-CoV-2.

In some embodiments, reference to SARS-CoV-2 includes reference to any SARS-CoV-2 isolate, SARS-CoV-2 variant, SARS-CoV-2 variant of interest (VOI), or SARS-CoV-2 variant of concern (VOC).

Accordingly, in some embodiments reference to SARS-CoV-2 includes reference to known variants such as the "UK variant", (known as 20I/501Y.V1, VOC 202012/01, or B.1.1.7), the "South African variant" (known as 20H/501Y.V2 or B.1.351) and the "Brazilian variant" (known as P.1).

The "UK variant" is characterized by the N501Y mutation in the receptor binding domain (RBD) of the spike protein at position 501. This variant also has several other mutations, including P681H near a furin cleavage site and a $^{69}/_{70}$ deletion that likely leads to a conformational change in the spike protein.

The "South African variant" is variant is characterized by multiple mutations in the spike protein, including K417N, E484K, N501Y. This variant does not contain the deletion at $^{69}/_{70}$.

The "Brazilian variant" is characterized by three mutations in the spike protein receptor binding domain: K417T, E484K, and N501Y.

Other variants include those with a D614G mutation in the spike protein, and the "Cluster 5" variant, also known as the "ΔFVI-spike" variant as identified in Denmark which is characterized by mutations including 69-70deltaHV (a deletion of the histidine and valine residues at the 69th and 70th position in the spike protein), Y453F, I692V, and S1147L.

The SARS-CoV-2 genome has been sequenced from over 150 isolates. One reference sequence is GenBank NC 045512 (Wang, C. et al. (2020) "The Establishment Of Reference Sequence for SARS-CoV-2 and variation analysis," *J. Med. Virol.* 2020 June; 92(6):667-674 (published online 13 Mar. 2020). Comparisons of the sequences of multiple isolates of the virus (MN988668 and NC 045512, isolated from Wuhan, China, and MN938384.1, MN975262.1, MN985325.1, MN988713.1, MN994467.1, MN994468.1, and MN997409.1) reveal greater than 95% identity. Accordingly, the methods described herein are applicable to SARS-CoV-2 variants having at 95%, 96%, 97%, 98%, or 99% sequence identity to a SARS-CoV-2 isolate.

In other embodiments the Coronavirus is a gamma coronavirus such as infectious bronchitis virus, or a delta coronavirus such as bulbul coronavirus HKU11 or porcine coronavirus.

6.2.2. Macrocyclic Lactones

Any macrocyclic lactone or combination of macrocyclic lactones is suitable for use in the methods and formulations described herein. Suitable macrocyclic lactones are known and can easily be obtained commercially or through synthesis techniques known in the art.

Typically, the macrocyclic lactone is an avermectin a milbemycin or a combination thereof. Avermectins and milbemycins contain a common macrocyclic lactone (ML) ring. The principal structural difference is that avermectins have sugar groups at C13 of the macrocyclic ring, whereas the milbemycins are protonated at C13. Moxidectin (a milbemycin) has other differences, including a methoxime at C23.

Avermectins are a group of pentacyclic 16-membered lactone compounds with. Abamectin is a mixture of avermectin $B_{1a}$(>90%) and avermectin $B_{1b}$(<10%). A-series compounds are methoxylated at the 5-position, whereas the B-series have an underivatized hydroxyl group at that position. The 1-subset compounds have an olefinic bond between C22 and C23; the 2-subset compounds possess a hydroxyl group at position 23 due to the hydration of the double bonds. They are considered to have very similar biological activities and toxicological properties. Overall avermectins are characterised among other macrocyclic lactones by the presence of a sugar substituent on the 13-position and of secondary butyl or isopropyl in the 25-position.

Ivermectin is a chemically reduced 22,23-dihydro derivative of abamectin, and is a mixture of 22,23-dihydroavermectin $B_{1a}$ (>90%) and 22,23-dihydro-avermectin $B_{1b}$ (<10%), differing from the components of abamectin by a single methylene group at the 26 position.

Eprinomectin is the amino-avermectin derived from avermectin B1 with modified terminal oleandrose moiety called 400-epiacetylamino-400-deoxy-avermectin B1. Doramectin is prepared by mutational biosynthesis and it has a closer structural similarity to abamectin than to Ivermectin. There is a different substituent at the 25 position without the dihydro modification at the 22-23 position. It differs from ivermectin by having a cyclohexyl group in the C25 position of the avermectin ring. Selamectin is a semisynthetic monosaccharide oxime derivative of doramectin. In terms of chemical structure and because of its monosaccharide, it is an intermediate between the disaccharide avermectins and milbemycins.

Milbemycin oxime is a naturally occurring compound isolated originally from *S. hygroscopicus* and contains the 16-membered macrocyclic lactone structure of milbemycin. Nematicidin is naturally occurring and can be derived from milbemycin. Moxidectin can be chemically derived from nematicidin by the addition of a methoxime moiety at C-23

Milbemycins are structurally similar to avermectins but are unglycosylated, lacking a bisoleandrosyl moiety in the 13-position. The milbemycins not only differ from the avermectins in lacking sugar groups at position-13, they also differ from the avermectin aglycones by being protonated at this position in contrast to the avermectin aglycones which are hydroxylated at this position. They also have an ethyl or a methyl at the 25-posi-tion. They can differ from one to another milbemycin by their substituent in the 5- and 25-position. Moxidectin has a substituted olefinicside chain at the 25-position and methoxime moiety at the 23-position which are both characteristics specific to this drug and not found in other commercial milbemycins or avermectins.

Suitable avermectins are well known in the art, for example, details of the avermectins ivermectin and abamectin, can be found in "Ivermectin and Abamectin", 1989, by M. H. Fischer and H. Mrozik, William C. Campbell, published by Springer Verlag., or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference is made to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336.

Macrocyclic lactones are either natural products or are semi-synthetic derivatives thereof and are well known in the art. For example suitable macrocyclic lactones can be found via references cited in "The Merck Index" 12.sup.th ed., S. Budavari, Ed., Merck & Co., Inc. Whitehouse Station, N.J. (1996) in addition to the "International Nonproprietary Names for Pharmaceutical Substances (INN)", WHO Drug Information, vol. 17, no. 4, pp. 263-286, (2003).

In some embodiments the avermectin is abamectin, dimadectin, doramectin, emamectin, eprinomectin, ivermectin, latidectin, lepimectin, selamectin or a combination thereof. In one embodiment the avermectin is ivermectin.

In some embodiments the milbemycin is milbemectin, milbemycin D, milbemycin oxime, moxidectin or nemadectin. In one embodiment the milbemycin is moxidectin.

In one embodiment the avermectin is a combination of ivermectin and the milbemycin is moxidectin.

In an embodiment the at least one macrocyclic lactone is a combination of at least one avermectin and at least one milbemycin. For example, the avermectin is selected from any one or more of abamectin, dimadectin, doramectin, emamectin, eprinomectin, ivermectin, latidectin, lepimectin, and selamectin; and the milbemycin is selected from any one or more of milbemectin, milbemycin D, milbemycin oxime, moxidectin and nemadectin.

In one embodiment the at least one macrocyclic lactone is a combination of ivermectin and moxidectin.

Additionally, where a macrocyclic lactone is referred to by name, this is intended to cover, where applicable, solvated as well as unsolvated forms of the compounds. Thus, each macrocyclic lactone (e.g. ivermectin or moxidectin) includes the hydrated or solvated form, as well as the non-hydrated and non-solvated forms. The term "solvate" is used herein to describe a molecular complex comprising the compound of the invention and one or more pharmaceutically acceptable solvent molecules, for example, ethanol. The term "hydrate" is employed when the solvent is water.

The term "pharmaceutically acceptable salt" refers to those salts which, within the scope of sound medical judgement, are suitable for use in contact with the tissues of humans and animals without undue toxicity, irritation, allergic response and the like, and are commensurate with a reasonable benefit/risk ratio. Pharmaceutically acceptable salts are well known in the art. S. M. Berge et al. describe pharmaceutically acceptable salts in detail in J. Pharmaceutical Sciences, 1977, 66:1-19. For a review on suitable salts, see Handbook of Pharmaceutical Salts: Properties, Selection, and Use by Stahl and Wermuth (Wiley-VCH, 2002). Methods for making pharmaceutically acceptable salts of compounds of the invention are known to one of skill in the art. The salts can be prepared in situ during the final isolation and purification of the compounds of the invention, or separately by reacting the free base function with a suitable organic acid. Suitable pharmaceutically acceptable acid addition salts of the compounds of the present invention may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, ascorbic, glucoronic, fumaric, maleic, pyruvic, alkyl sulfonic, arylsulfonic, aspartic, glutamic, benzoic, anthranilic, mesylic, methanesulfonic, salicylic, p-hydroxybenzoic, phenylacetic, mandelic, ambonic, pamoic, pantothenic, sulfanilic, cyclohexylaminosulfonic, stearic, algenic, β-hydroxybutyric, galactaric, and galacturonic acids. Suitable pharmaceutically acceptable base addition salts of the compounds of the present invention include metallic salts made from lithium, sodium, potassium, magnesium, calcium, aluminium, and zinc, and organic salts made from organic bases such as choline, diethanolamine, morpholine. Alternatively, suitable pharmaceutically acceptable base addition salts of the compounds of the present invention include organic salts made from N,N'-dibenzylethylenediamine, chloroprocaine, choline, diethanolamine, ethylenediamine, meglumine (N methylglucamine), procaine, ammonium salts, quaternary salts such as tetramethylammonium salt, amino acid addition salts such as salts with glycine and arginine. In the case of compounds that are solids, it will be understood by those skilled in the art that the inventive compounds, agents and salts may exist in different crystalline or polymorphic forms, all of which are intended to be within the scope of the present invention and specified macrocyclic lactones.

The term "stereoisomer" as used herein refers to any two or more isomers that have the same molecular constitution and differ only in the three dimensional arrangement of their atomic groupings in space. Stereoisomers may be diastereoisomers or enantiomers. It will be recognized that the compounds described herein may possess asymmetric centres and are therefore capable of existing in more than one stereoisomeric form. The invention thus also relates to compounds in substantially pure isomeric form at one or more asymmetric centres e.g., greater than about 90% ee (enantiomeric excess), such as about 95% or 97% ee or greater than 99% ee, as well as mixtures, including racemic mixtures, thereof. Such isomers may be naturally occurring or may be prepared by asymmetric synthesis, for example using chiral intermediates, or by chiral resolution.

In certain embodiments, the macrocyclic lactone can be a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent.

It will be apparent to those skilled in the art that a general reference to "a macrocyclic lactone" or reference to a macrocyclic lactone by name (e.g., ivermectin or moxidectin) refers to compounds and salts, hydrates, solvates, tautomers or stereoisomers thereof unless expressly stated otherwise.

In order that the present technology may be more clearly understood, preferred embodiments will be described with reference to the following examples and drawings.

7. EXAMPLES

Example 1: Cell Culture, Viral Infection and Drug Treatment

Vero/hSLAM cells were maintained in Earle's Minimum Essential Medium (EMEM) containing 7% Fetal Bovine Serum (FBS) (Bovogen Biologicals, Keilor East, AUS) 2 mM L-Glutamine, 1 mM Sodium pyruvate, 1500 mg/L sodium bicarbonate, 15 mM HEPES and 0.4 mg/ml geneticin at 37° C., 5% $CO_2$. Cells were seeded into 12-well tissue culture plates 24 h prior to infection with SARS-CoV-2 (Australia/VIC01/2020 isolate) at an MOI of 0.1 in infection media (as per maintenance media but containing only 2% FBS) for 2 h. Media containing inoculum was removed and replaced with 1 mL fresh media (2% FBS) containing Ivermectin at the indicated concentrations or DMSO alone and incubated as indicated for 0-3 days. At the appropriate time point, cell supernatant was collected and spun for 10 min at 6,000 g to remove debris and the supernatant transferred to fresh collection tubes. The cell monolayers were collected by scraping and resuspension into 1 mL fresh media (2% FBS). Toxicity controls were set up in parallel in every experiment on uninfected cells.

Example 2: Generation of SARS-CoV-2 cDNA

RNA was extracted from 200 μL aliquots of sample supernatant or cell suspension using the QIAamp 96 Virus QIAcube HT Kit (Qiagen, Hilden, Germany) and eluted in 60 μL. Reverse transcription was performed using the Bio-Line SensiFAST cDNA kit (Bioline, London, United Kingdom), total reaction mixture (20 μL, containing 10 μL of RNA extract, 4 μl of 5× TransAmp buffer, 1 μl of Reverse Transcriptase and 5 μl of Nuclease free water. The reactions were incubated at 25° C. for 10 min, 42° C. for 15 min and 85° C. for 5 min.

Example 3: Detection of SARS-CoV-2 Using a TaqMan Real-Time RT-PCR Assay

TaqMan RT-PCR assay were performed using 2.5 μl cDNA, 10 μl Primer Design PrecisonPLUS qPCR Master Mix 1 μM Forward (5'-AAA TTC TAT GGT GGT TGG CAC AAC ATG TT-3'), 1 μM Reverse (5'-TAG GCA TAG CTC TRT CAC AYT T-3') primers and 0.2 μM probe (5'-FAM-TGG GTT GGG ATT ATC-MGBNFQ-3') targeting the BetaCoV RdRp (RNA-dependent RNA polymerase) gene or Forward (5'-ACA GGT ACG TTA ATA GTT AAT AGC GT-3'), 1 μM Reverse (5'-ATA TTG CAG CAG TAC GCA CAC A-3') primers and 0.2 μM probe (5'-FAM-ACA CTA GCC ATC CTT ACT GCG CTT CG-286 NFQ-3') targeting the BetaCoV E-gene. Real-time RT-PCR assays were performed on an Applied Biosystems ABI 7500 Fast real-time PCR machine (Applied Biosystems, Foster City, Calif., USA) using cycling conditions of 95° C. for 2 min, 95° C. for 5s, 60° C. for 24s. SARS-CoV-2 cDNA (Ct-28)

was used as a positive control. Calculated Ct values were converted to fold-reduction of treated samples compared to control using the ΔCt method (fold changed in viral RNA=$2^{\Delta Ct}$) and expressed as % of DMSO alone sample. $IC_{50}$ values were fitted using 3 parameter dose response curves in GraphPad prism.

Example 4: Effect of Ivermectin and Moxidectin

Figure 1:
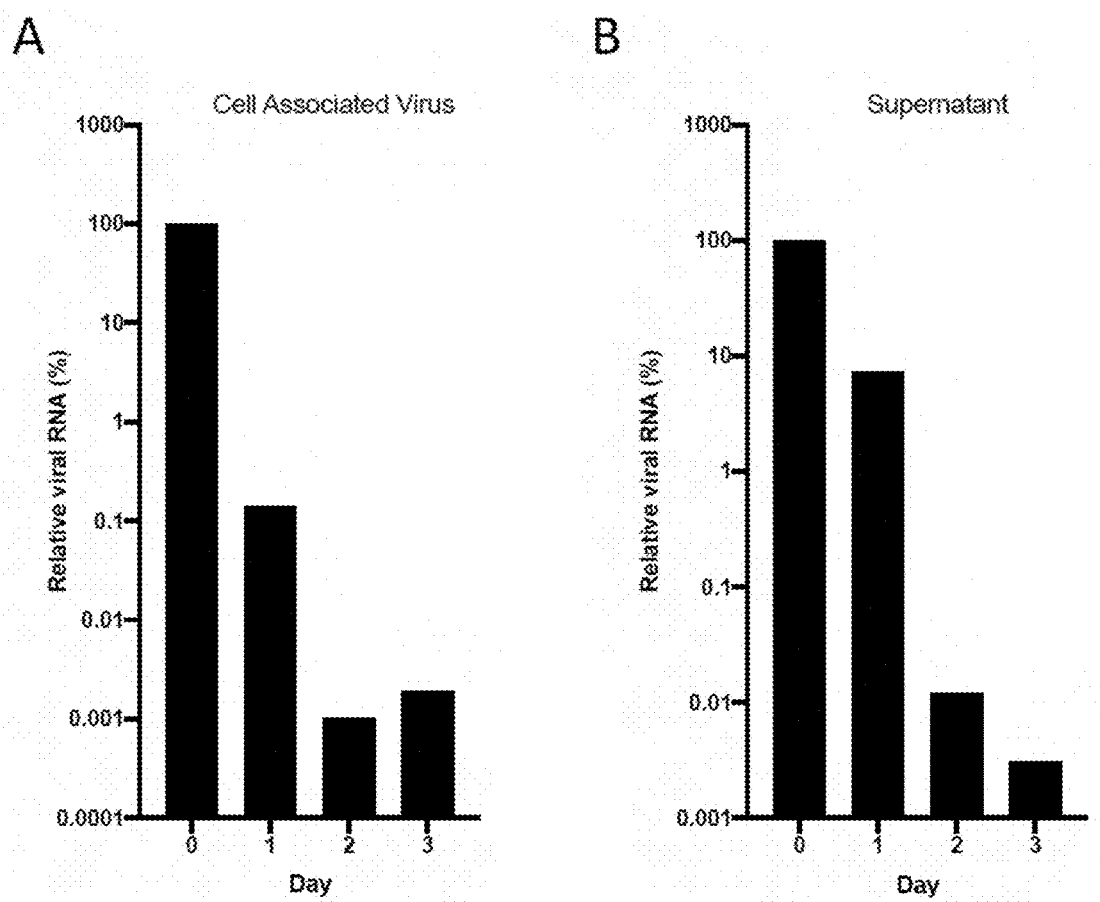
Figure 1:
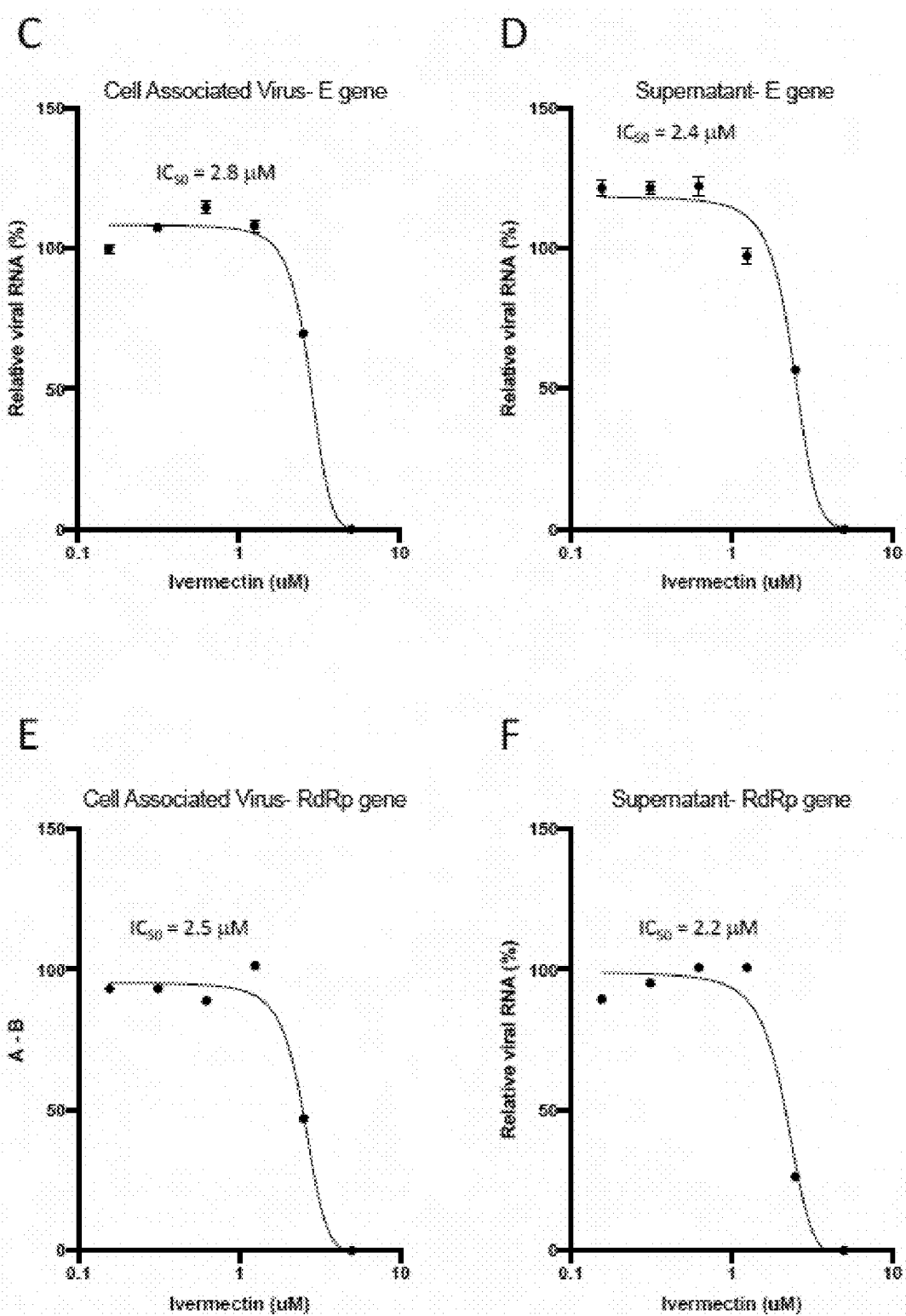

To test the antiviral activity of ivermectin towards SARS-CoV-2, Vero/hSLAM cells were infected with SARS-CoV-2 isolate Australia/VIC01/2020 at an MOI of 0.1 for 2 h, followed by the addition of 5 μM ivermectin. Supernatant and cell pellets were harvested at days 0-3 and analysed by RT-PCR for the replication of SARS-CoV-2 RNA (FIG. 1, panels A/B). At 24 h, there was a 93% reduction in viral RNA present in the supernatant (indicative of released virions) of samples treated with ivermectin compared to the vehicle DMSO Similarly a 99.8% reduction in cell-associated viral RNA (indicative of unreleased and unpackaged virions) was observed with ivermectin treatment. By 48h this effect increased to a 99.98/99.99% reduction of viral RNA in ivermectin-treated compared to control samples, indicating that ivermectin treatment resulted in the effective loss of essentially all viral material by 48 h. Consistent with this idea, no further reduction in viral RNA was observed at 72 h. No toxicity of ivermectin was observed at any of the time points tested, in either the sample wells or parallel drug alone samples.

To further determine the effectiveness of ivermectin, cells infected with SARS-CoV-2 were treated with serial dilutions of ivermectin 2 h post infection and supernatant and cell pellets collected for RT-PCR at 48 h (FIG. 1, panels C/D). As above, a >5000 reduction in viral RNA was observed in both supernatant and cell pellets from samples treated with 5 μM ivermectin at 48 h, equating to a 99.98% reduction in viral RNA in these samples. Again, no toxicity was observed with ivermectin at any of the concentrations tested. The $IC_{50}$ of ivermectin treatment was determined to be 2.8 μM (FIG. 1, panel C) and 2.4 μM (FIG. 1, panel D). Underlining the fact that the assay indeed specifically detected SARS-CoV-2, RT-PCR experiments were repeated using primers specific for the viral RdRp gene (FIG. 1, panels E/F) rather than the E gene (above), with nearly identical results observed for both released (supernatant) and cell-associated virus. In particular the $IC_{50}$ of ivermectin treatment was determined to be 2.5 μM (FIG. 1, panel E) and 2.2 μM (FIG. 1, panel F).

Figure 2:
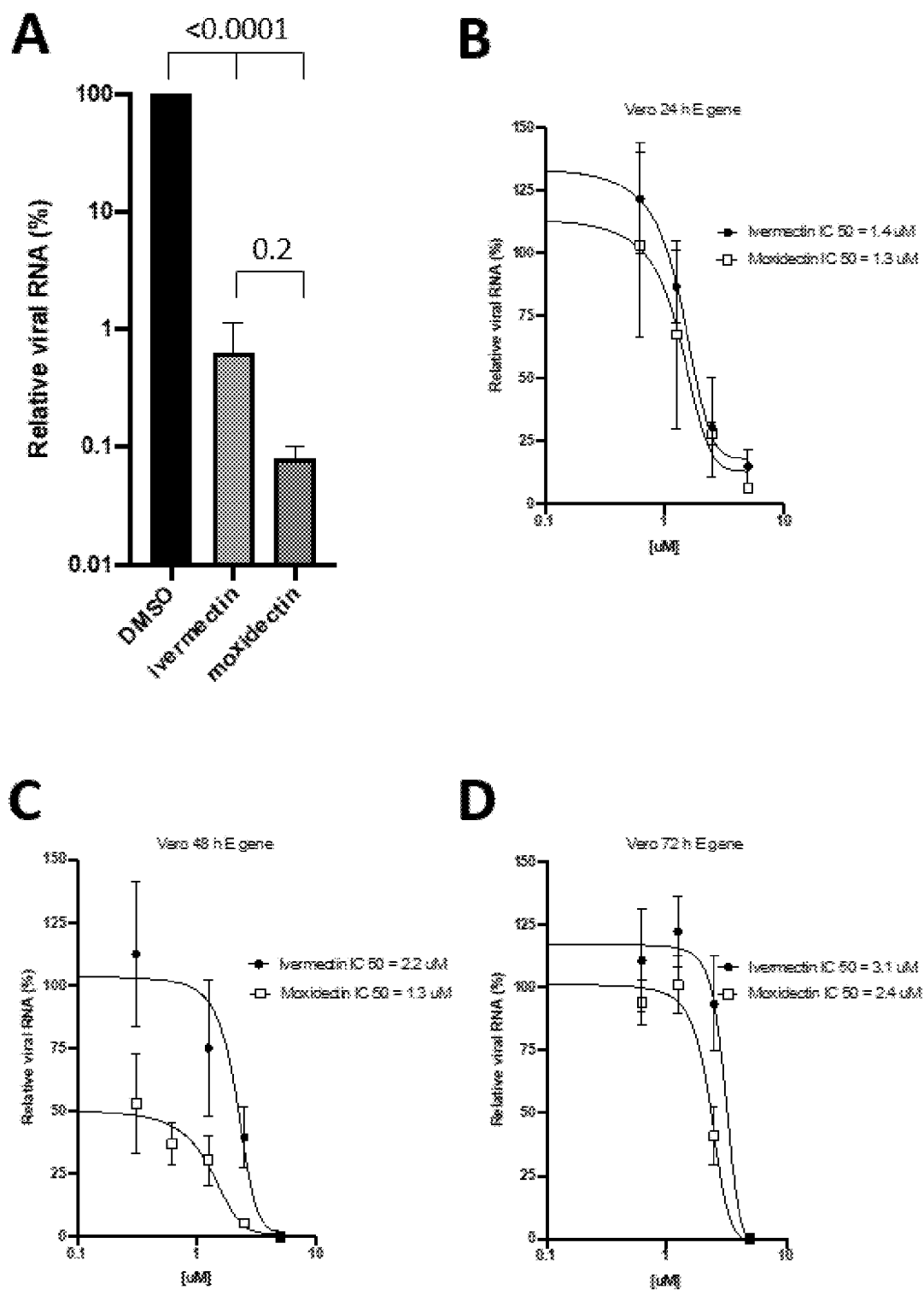

To test the antiviral activity of moxidectin towards SARS-CoV-2 and compare the activity to that of ivermectin, Vero/hSLAM cells were infected with SARS-CoV-2 isolate Australia/VIC01/2020 at an MOI of 0.1 for 2 h, followed by the addition of 5 μM ivermectin or 5 μM moxidectin. Supernatant and cell pellets (n=3, biological replicates) were harvested at 48 hours for quantitation of viral load using real-time PCR using probes against the SARS-CoV-2 E gene. Results represent mean±SEM (n=3). p values determined by t-test with Welch's correction (FIG. 2, panel A).

Vero/hSLAM cells infected were infected with SARS-CoV-2 clinical isolate Australia/VIC01/2020 (MOI=0.01) for 2 h prior to addition of vehicle (DMSO), ivermectin (solid squares) or moxidectin (open squares) at the indicated concentrations. Supernatant was analysed as above for the SARS-CoV-2 E gene at 24 h (FIG. 2, panel B), 48 h (FIG. 2, panel C) or 72 h (FIG. 2, panel D). Results represent mean±SEM (n=3). Calculated $IC_{50}$ values from FIG. 2, panel B are 1.4 μM for ivermectin and 1.3 μM for moxidectin. Calculated $IC_{50}$ values from FIG. 2, panel C are 2.2 μM for ivermectin and 1.3 μM for moxidectin. Calculated $IC_{50}$ values from FIG. 2, panel D are 3.1 μM for ivermectin and 2.4 μM for moxidectin. That is, at 48 h, there was a 99.5% reduction in viral RNA present in the supernatant (indicative of released virions) of samples treated with ivermectin, and a 99.9% reduction in viral RNA present in the supernatant of samples treated with moxidectin, compared to the vehicle DMSO. No toxicity of moxidectin was observed at any of the time points tested, in either the sample wells or parallel drug alone samples.

Taken together these results confirm that ivermectin and moxidectin are potent antivirals able to contain the SARS-CoV-2 clinical isolate, with a single dose of either able to control viral replication within 24 to 48 hours, likely through effects on the IMP α/β1 mediated nuclear transport of viral proteins. Ivermectin and moxidectin have established safety profiles for human use and are FDA-approved for treating a number of parasitic infections in humans making them, and other macrocyclic lactones, an enticing possibility as a broad-spectrum antiviral.

Figure 3:
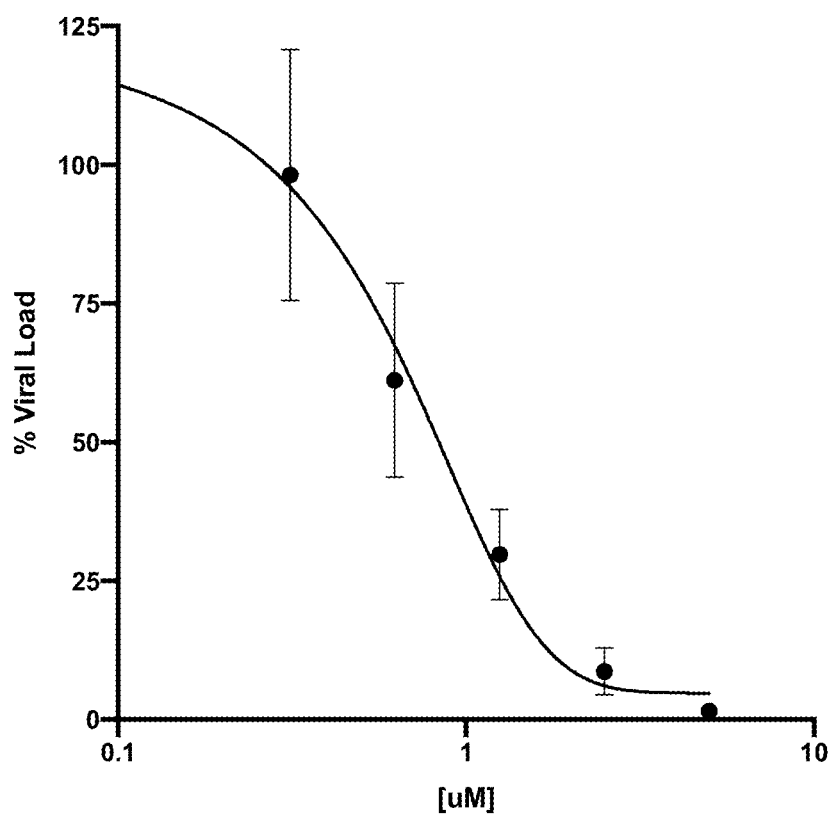
FIG. 3 illustrates that ivermectin reduces the viral load of CALU-3 (human lung) cells infected with SARS-CoV-2 clinical isolate Australia/VIC01/2020

Example 5: Ivermectin SARS-CoV-2 Anti-Viral Activity is Enhanced in Human Lung Cells CALU-3 (human lung) cells were infected with SARS-CoV-2 clinical isolate Australia/VIC01/2020 (MOI=0.01) for 2 h prior to addition of vehicle (DMSO) or Ivermectin at the indicated concentrations indicated in FIG. 3. Samples were taken 24 h post infection for quantitation of viral load using real-time PCR of supernatant. The results illustrated in FIG. 3 represent mean±SD (n=6) relative to DMSO alone. Three parameter dose response curves were fitted using GraphPad prism to determine an $IC_{50}$ value of 0.42 μM.

Average $IC_{50}$ values for CALU-3 cells compared to Vero/hSLAM cells assayed under the same conditions are shown in Table 1 which indicates that ivermectin SARS-CoV-2 anti-viral activity is enhanced in human lung cells compared to Vero/hSLAM cells.

TABLE 1

| $IC_{50}$ values for CALU-3 cells compared to Vero/hSLAM cells. | |
|---|---|
| Cell Line | $IC_{50}$ +/− SEM (n*) |
| Vero/hSLAM | 2.37 +/− 0.23 (7) |
| CALU-3 | 0.41 +/− 0.15 (4) |

(*n) = number of independent experiments

Figure 4:
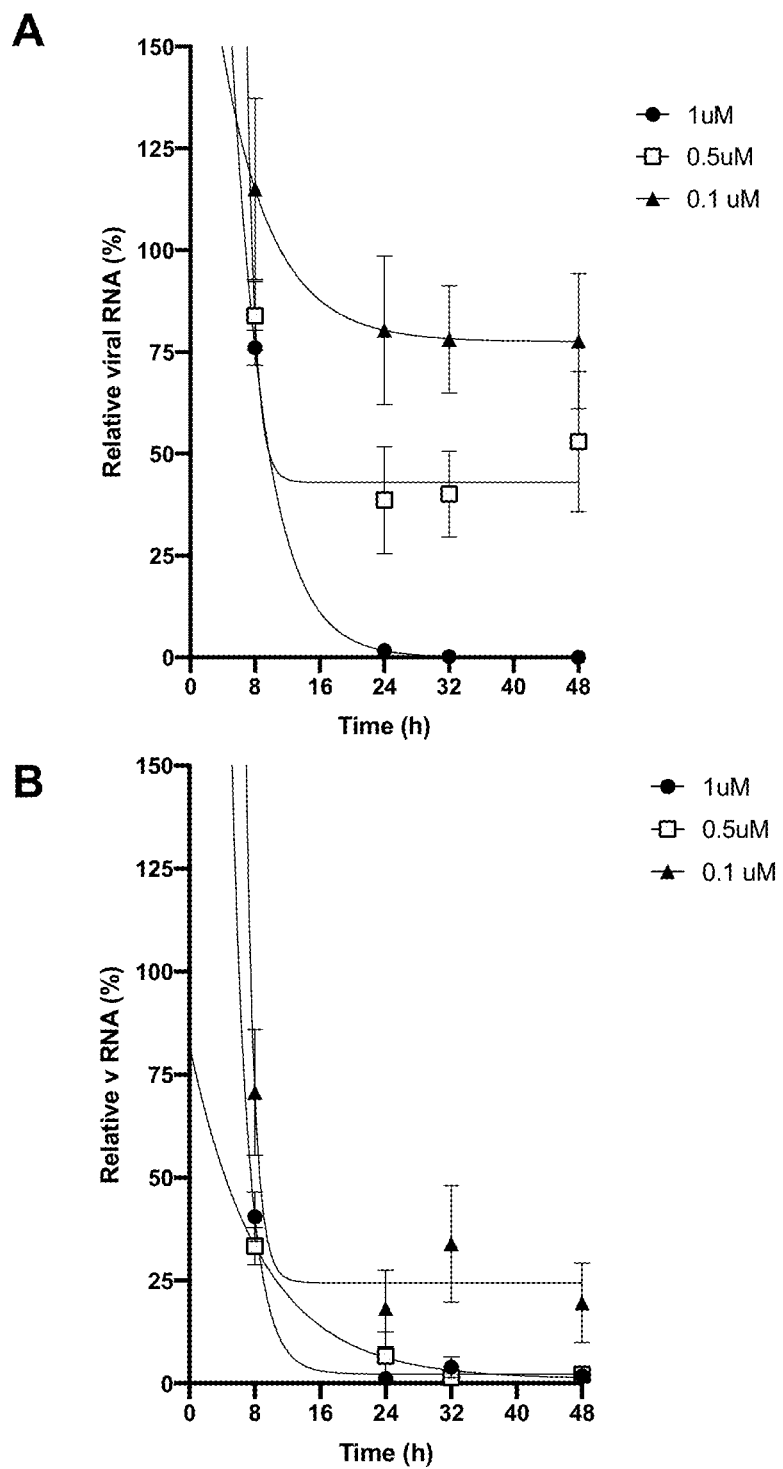
FIG. 4 illustrates that multidose ivermectin or moxidectin treatment enhances SARS-CoV-2 anti-viral activity compared to single treatment. Vero/hSLAM (A/C) or CALU-3 (B/D) cells were infected with SARS-CoV-2 clinical isolate Australia/VIC01/2020 prior to addition of vehicle (DMSO), ivermectin (A/B), or moxidectin (C/D) at the indicated concentrations.
Figure 4:
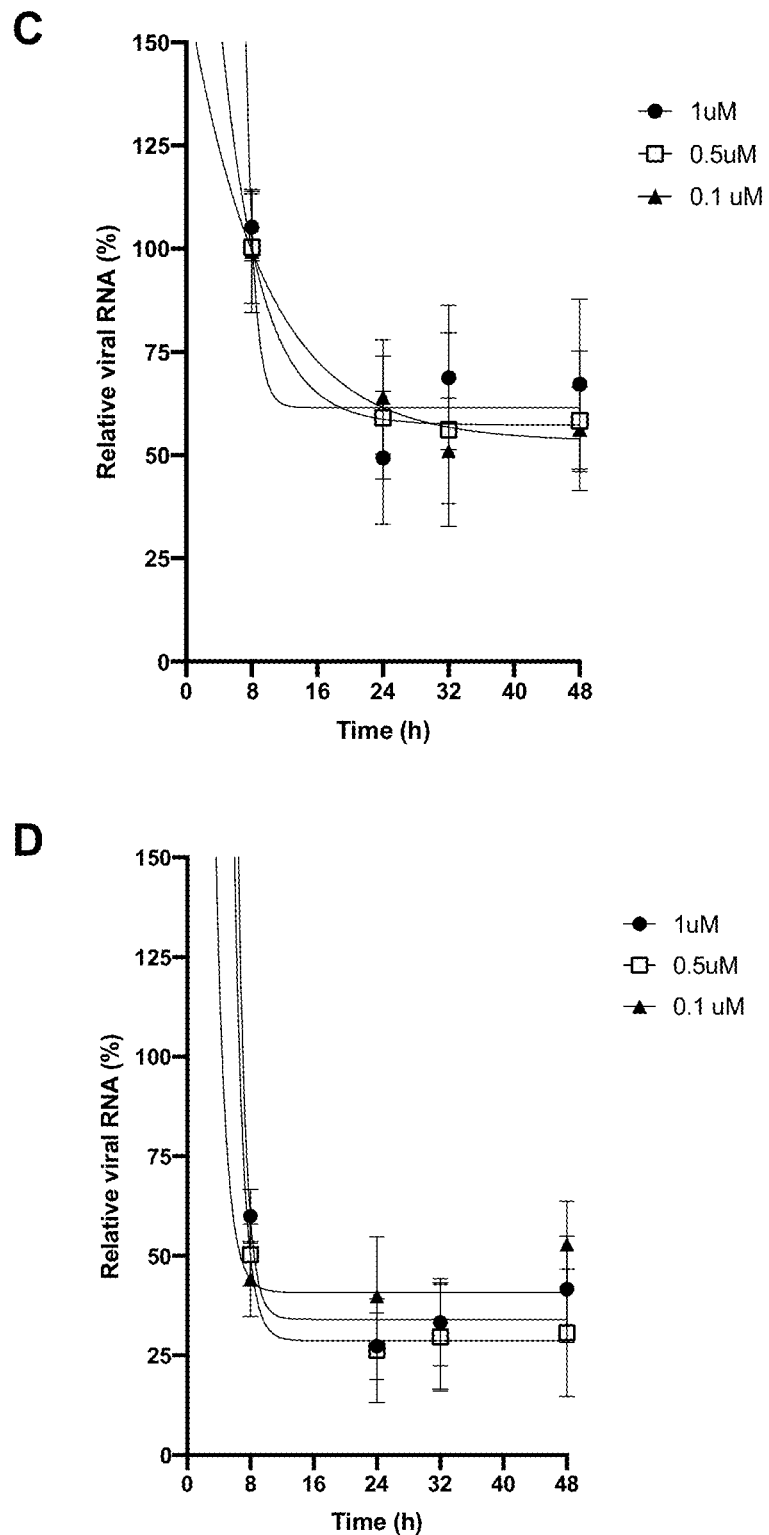

Example 6: Multidose Ivermectin or Moxidectin Enhances SARS-CoV-2 Anti-Viral Activity Vero/hSLAM cells (FIG. 4, panels A/C) or CALU-3 (FIG. 4, panels B/D) cells were infected with SARS-CoV-2 clinical isolate Australia/VIC01/2020 (MOI=0.01) for 2 h prior to addition of vehicle (DMSO), Ivermectin (A/B) or Moxidectin (C/D) at the concentrations indicated in FIG. 4. Supernatant was harvested at 8, 24, 32 and 48 h and replaced with fresh media containing the same concentration of drug or DMSO. Samples were quantitated for viral load using real-time PCR. Results represent mean±SD (n=6) relative to DMSO alone under the same conditions. Three parameter dose response curves were fitted using GraphPad prism. The data presented in FIG. 4 are single typical graphs from a series of two similar experiments.

Example 7: Ivermectin and Moxidectin have Prophylactic Anti-Viral Activity Against SARS-CoV-2

Figure 5:
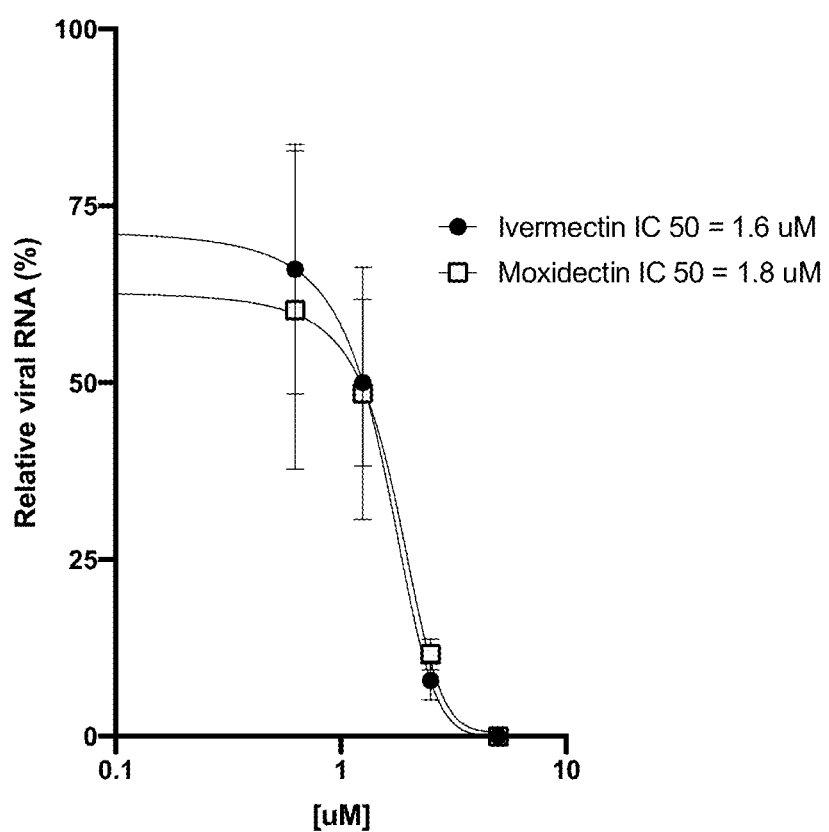
FIG. 5 illustrates that ivermectin and moxidectin have prophylactic anti-viral activity against SARS-CoV-2 in Vero/hSLAM cells. Vero/hSLAM cells were pre-treated with DMSO, ivermectin or moxidectin at the indicated concentrations for 2 h prior to infection with SARS-CoV-2 (MOI=0.01) for 2 h in the presence of DMSO or drugs.

Vero/hSLAM cells were pre-treated with DMSO, ivermectin or Moxidectin at the indicated concentrations for 2 h prior to infection with SARS-CoV-2 (MOI=0.01) for 2 h in the presence of DMSO or drugs. Samples were washed post-adsorption and incubated in the fresh media containing DMSO or drugs for 48 h before quantitation of viral load using real-time PCR of supernatant. The results shown in FIG. 5 represent mean±SD (n=6) relative to DMSO alone. Three parameter dose response curves were fitted using GraphPad prism to determine $IC_{50}$ value of 1.6 µM for ivermectin and 1.8 µM for moxidectin. Average $IC_{50}$ values for CALU-3 cells compared to Vero/hSLAM cells assayed under the same conditions are shown (Table, right, n=independent experiments).

TABLE 2

$IC_{50}$ values for Vero/hSLAM cells treated prophylactically with Ivermectin compared to Moxidectin.

| Drug | IC50 +/− SEM (n*) |
|---|---|
| Ivermectin | 1.73 +/− 0.29 (3) |
| Moxidectin | 1.66 +/− 0.23 (3) |

(*n) = number of independent experiments

Example 8: Ivermectin and Moxidectin are Effective Anti-Viral Inhibitors of the Seasonal Coronavirus 229E Huh-7 cells were infected with 229E (MOI=0.01) for 2 h prior to addition of vehicle (DMSO), Ivermectin (FIG. 6, panel A) or Moxidectin (FIG. 6, panel B) at the indicated concentrations. Samples were taken 48 h post infection for quantitation of viral load using real-time PCR of supernatant. Results represent mean±SD (n=6) relative to DMSO alone. Three parameter dose response curves were fitted using GraphPad prism to determine $IC_{50}$ values of 0.18 µM for ivermectin, and 0.24 µM for moxidectin.

For assessment of prophylactic potential Huh-7 cells were pre-treated with DMSO or ivermectin at the indicated concentrations for 2 h prior to infection with 229E (MOI=0.01) for 2 h in the presence of DMSO or ivermectin (FIG. 6, panel C). Samples (n=5) were washed post-adsorption and incubated in the fresh media containing DMSO or ivermectin for 48 h before quantitation of viral load as above. Three parameter dose response curves were fitted using GraphPad prism to determine an $IC_{50}$ value of 2.06 µM for ivermectin.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of treating a coronavirus infection in a human subject in need thereof, the method comprising administering to the human subject a therapeutically effective amount of at least one macrocyclic lactone or a salt, hydrate, solvate, tautomer, or stereoisomer thereof, wherein the at least one macrocyclic lactone is ivermectin, moxidectin, or both ivermectin and moxidectin.

2. The method of claim 1, wherein the method reduces the level of detectable coronavirus in the human subject by at least 50%.

3. The method of claim 1, wherein the method reduces the level of detectable coronavirus in the human subject by at least 70%.

4. The method of claim 2, wherein the method reduces the level of detectable coronavirus in the human subject over a period of 1 to 3 days after administration of the macrocyclic lactone or a salt, hydrate, solvate, tautomer, or stereoisomer thereof.

5. The method of claim 1, wherein the coronavirus is coronavirus 229E, coronavirus NL63, coronavirus OC43, SARS-CoV, MERS-CoV, SARS-CoV-2, or a variant thereof.

6. The method of claim 1, wherein the coronavirus is SARS-CoV-2 or a SARS-CoV-2 variant.

7. The method of claim 1, wherein the at least one macrocyclic lactone or a salt, hydrate, solvate, tautomer, or stereoisomer thereof is administered to the human subject at a dose of about 0.1 mg/kg to about 1.0 mg/kg.

8. The method of claim 1, wherein the method reduces the level of detectable coronavirus in the human subject by at least 80%.

9. The method of claim 1, wherein the method reduces the level of detectable coronavirus in the human subject by at least 90%.

10. The method of claim 2, wherein the method reduces the level of detectable coronavirus in the human subject over a period of 3 or more days after administration of the macrocyclic lactone or a salt, hydrate, solvate, tautomer, or stereoisomer thereof.

11. A method of inhibiting a coronavirus in a human subject in need thereof, the method comprising administering to the human subject a therapeutically effective amount of at least one macrocyclic lactone or a salt, hydrate, solvate, tautomer, or stereoisomer thereof, wherein the at least one macrocyclic lactone is ivermectin, moxidectin, or both ivermectin and moxidectin.

12. The method of claim 11, wherein the method reduces the level of detectable coronavirus in the human subject by at least 50%.

13. The method of claim 11, wherein the method reduces the level of detectable coronavirus in the human subject by at least 70%.

14. The method of claim 12, wherein the method reduces the level of detectable coronavirus in the human subject over a period of 1 to 3 days after administration of the macrocyclic lactone or a salt, hydrate, solvate, tautomer, or stereoisomer thereof.

15. The method of claim 11, wherein the coronavirus is coronavirus 229E, coronavirus NL63, coronavirus OC43, SARS-CoV, MERS-CoV, SARS-CoV-2, or a variant thereof.

16. The method of claim 11, wherein the coronavirus is SARS-CoV-2 or a SARS-CoV-2 variant.

17. The method of claim 11, wherein the at least one macrocyclic lactone or a salt, hydrate, solvate, tautomer, or stereoisomer thereof is administered to the human subject at a dose of about 0.1 mg/kg to about 1.0 mg/kg.

18. The method of claim 11, wherein the method reduces the level of detectable coronavirus in the human subject by at least 80%.

19. The method of claim 11, wherein the method reduces the level of detectable coronavirus in the human subject by at least 90%.

20. The method of claim 12, wherein the method reduces the level of detectable coronavirus in the human subject over a period of 3 or more days after administration of the macrocyclic lactone or a salt, hydrate, solvate, tautomer, or stereoisomer thereof.

21. A method of preventing antibody-dependent enhanced (ADE) coronavirus infection in a human subject, comprising administering to the human subject a therapeutically effective amount of at least one macrocyclic lactone, or a salt, hydrate, solvate, tautomer, or stereoisomer thereof, wherein the at least one macrocyclic lactone is ivermectin, moxidectin, or both ivermectin and moxidectin.

22. The method of claim 21, wherein the method reduces the level of detectable coronavirus in the human subject by at least 50%.

23. The method of claim 21, wherein the method reduces the level of detectable coronavirus in the human subject by at least 70%.

24. The method of claim 22, wherein the method reduces the level of detectable coronavirus in the human subject over a period of 1 to 3 days after administration of the macrocyclic lactone or a salt, hydrate, solvate, tautomer, or stereoisomer thereof.

25. The method of claim 21, wherein the coronavirus is coronavirus 229E, coronavirus NL63, coronavirus OC43, SARS-CoV, MERS-CoV, SARS-CoV-2, or a variant thereof.

26. The method of claim 21, wherein the coronavirus is SARS-CoV-2 or a SARS-CoV-2 variant.

27. The method of claim 21, wherein the at least one macrocyclic lactone or a salt, hydrate, solvate, tautomer, or stereoisomer thereof is administered to the human subject at a dose of about 0.1 mg/kg to about 1.0 mg/kg.

28. The method of claim 21, wherein the method reduces the level of detectable coronavirus in the human subject by at least 80%.

29. The method of claim 21, wherein the method reduces the level of detectable coronavirus in the human subject by at least 90%.

30. The method of claim 22, wherein the method reduces the level of detectable coronavirus in the human subject over a period of 3 or more days after administration of the macrocyclic lactone or a salt, hydrate, solvate, tautomer, or stereoisomer thereof.

* * * * *